(12) United States Patent
Mutafyan

(10) Patent No.: US 12,310,646 B1
(45) Date of Patent: May 27, 2025

(54) ENDOSCOPIC BIPOLAR FORCEPS WITH VARIABLE TEMPERATURE CONTROL

(71) Applicant: Gevorg Mutafyan, Glendale, CA (US)

(72) Inventor: Gevorg Mutafyan, Glendale, CA (US)

( * ) Notice: Subject to any disclaimer, the term of this patent is extended or adjusted under 35 U.S.C. 154(b) by 0 days.

(21) Appl. No.: 18/819,077

(22) Filed: Aug. 29, 2024

(51) Int. Cl.
| | |
|---|---|
| *A61B 18/08* | (2006.01) |
| *A61B 18/00* | (2006.01) |
| *A61B 17/00* | (2006.01) |
| *A61B 17/295* | (2006.01) |

(52) U.S. Cl.
CPC .. *A61B 18/085* (2013.01); *A61B 2017/00424* (2013.01); *A61B 17/295* (2013.01); *A61B 2018/0063* (2013.01); *A61B 2018/00642* (2013.01); *A61B 2018/00714* (2013.01); *A61B 2018/00875* (2013.01); *A61B 2018/00922* (2013.01)

(58) Field of Classification Search
None
See application file for complete search history.

(56) References Cited

U.S. PATENT DOCUMENTS

| | | | | | |
|---|---|---|---|---|---|
| 5,443,463 | A | * | 8/1995 | Stern | A61N 1/06 606/51 |
| 5,626,578 | A | * | 5/1997 | Tihon | A61B 18/1442 606/50 |
| 5,797,938 | A | * | 8/1998 | Paraschac | A61B 18/1445 606/177 |
| 6,007,570 | A | * | 12/1999 | Sharkey | A61N 1/06 607/101 |
| 2002/0062123 | A1 | * | 5/2002 | McClurken | A61B 18/1442 606/34 |
| 2003/0125734 | A1 | * | 7/2003 | Mollenauer | A61B 18/085 606/51 |
| 2006/0052779 | A1 | * | 3/2006 | Hammill | A61B 18/1442 606/51 |
| 2011/0066150 | A1 | * | 3/2011 | Beller | A61B 18/1477 606/41 |
| 2017/0181765 | A1 | * | 6/2017 | Riestenberg | A61B 17/29 |

* cited by examiner

*Primary Examiner* — Michael F Peffley
*Assistant Examiner* — Nicholas S Borsch
(74) *Attorney, Agent, or Firm* — Cynthia S. Lamon; Lamon Patent Services

(57) ABSTRACT

An endoscopic bipolar forceps device features a housing equipped with an ergonomic handle and a movable handle assembly that is pivotally connected to the housing. The device includes a shaft extending from the housing, with an end effector assembly that can be detached from the distal end of the shaft. The end effector assembly comprises opposing jaw members: one with variable temperature electrode heat bars and the other with recessed areas designed to accept these bars. Configuration enables secure grasping and manipulation of tissue. A trigger on the handle assembly allows the jaws to transition between open and closed positions. The device is also equipped with a temperature control unit connected via a control cable to regulate the temperatures of the electrode heat bars. The electrode heat bars are capable of operating at different temperatures, and the jaws can be configured to be either curved or flat for enhanced performance.

13 Claims, 8 Drawing Sheets

ENDOSCOPIC BIPOLAR FORCEPS WITH VARIABLE TEMPERATURE CONTROL

BACKGROUND OF INVENTION

1. Field of the Invention

The present disclosure relates to an electrosurgical forceps and more particularly, to an endoscopic bipolar electrosurgical forceps with variable heating element selection and temperature control for manipulating, clamping, sealing, and cutting tissue with a single tool.

2. Discussion of the State of the Art

The following description includes information that may be useful in understanding the present disclosure. It is not an admission that any of the information provided herein is prior art or relevant to the present disclosure, or that any publication specifically or implicitly referenced is prior art.

Endoscopic bipolar forceps are widely used in minimally invasive surgical procedures to grasp, manipulate, and seal tissue. These devices use bipolar electrical energy to create a tissue seal by coagulating and fusing tissue together. Despite their widespread use, current vein tissue closing and burning tools have notable limitations. One significant drawback is their rudimentary design, which lacks the capability to vary the temperature of the tool's heating elements. This limitation is critical because different tissues and tissue sizes require different temperatures for effective sealing and coagulation. When a single, fixed temperature is applied across varying tissue types, the result can be suboptimal, leading to ineffective sealing, increased procedure time, and potentially higher rates of intra-operative and post-operative complications.

Traditional endoscopic forceps often face limitations in terms of temperature control, sealing landscape, handling, and versatility. Existing devices typically provide either inadequate control overheat application or lack the ergonomic design needed for comfortable and efficient use during extended procedures. Moreover, conventional forceps sealing tools may struggle with consistent sealing and cutting, which are essential for various surgical procedures. In the current art, a medical professional may need to repeatedly seal a same area of tissue to prevent bleeding due to frequent failures and other factors. Repeated sealing may cause a general lack of confidence in the tool by the operator and extended surgical times which also may cause unnecessary complications.

Furthermore, existing devices often have a heating bar, or bars positioned in a manner that enable trapping of fat cells along with the target vessel and other types of tissue making sealing difficult due to increased resistance of the grasped tissues and poor current penetration to the target vessel. This design flaw inhibits the proper closure of tissue, as the trapped fat cells prevent the necessary direct contact and uniform heating of the tissue. Consequently, this can result in incomplete seals, increased risk of tissue damage, instances of bleeding during sealing and prolonged recovery times for patients. These shortcomings highlight the need for an improved endoscopic bipolar forceps that incorporates variable temperature settings to accommodate different tissue types and sizes and features a design that delivers energy directly to the target vessel (tissue) and minimizes the trapping of fat cells or other obstructive tissue, thereby decreasing resistance and ensuring more efficient and reliable tissue sealing.

SUMMARY OF INVENTION

The present disclosure overcomes one or more shortcomings of the prior art and provides additional advantages discussed throughout the present disclosure. Additional features and advantages are realized through the techniques of the present disclosure. Other embodiments and aspects of the disclosure are described in detail herein and are considered a part of the claimed disclosure.

In an aspect, the present disclosure relates to an endoscopic bipolar forceps device that features a robust design comprising a housing unit equipped with a handle that includes an ergonomic grip to ensure safe and easy handling during surgical operations. The device incorporates a movable handle assembly that is pivotally connected to the housing, allowing for precise control of the shaft extending from the housing. This configuration facilitates the operation of an end effector assembly, which is detachably attached to the distal end of the shaft, enhancing the versatility and functionality of the device.

The endoscopic bipolar forceps device includes an end effector assembly, which includes a pair of opposing jaw members. One jaw member is designed with a plurality of variable temperature electrode heat bars disposed on its inner facing surface, while the opposing jaw member features a series of recessed areas on its inner facing surface. These recessed areas are configured to accept the corresponding electrode heat bars when the jaw members are in a closed position, allowing an improved compression of the tissues held in the jaws which minimizes fat content next to and interfering with the target vessel. The symmetrical arrangement of the electrode heat bars and recessed areas ensures maximum compression and close direct contact to the vessel. Additionally, a typical fat cell may be 0.1 mm in diameter with some being twice that size, and others half that size, so the size ranges from 0.05 mm to 0.2 mm. In various embodiments of the present invention open space between the heat bars may be within this range so when bars are introduced into recesses of the opposing jaw member fat cells may not be trapped in these open spaces but are moved out of the way by compression of the bars.

In an exemplary embodiment, the device is equipped with a control cable integrated into the housing, which is detachably connected to a temperature control unit. This unit is responsible for providing controlled electric power to the electrode heat bars, allowing for precise regulation of their temperature. The temperature control unit enables the operator to adjust the heat levels of the individual electrode heat bars, providing the flexibility needed to cater to various surgical requirements and tissue types. This feature is particularly beneficial for achieving optimal results in complex surgical procedures. In one embodiment, the outer bar setting may remain standard while the inner bars may have higher current settings to provide assured seal in the middle of the jaw without lateral thermal spread.

Each jaw member is operatively coupled to a pivoting member, which allows the jaw members to transition between open and closed positions. In the closed position, the jaw members are capable of securely grasping tissue, while in the open position, the tissue is released. This mechanism ensures precise and controlled movement of the jaw members, enhancing the efficiency and effectiveness of the surgical process.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF DRAWINGS

The embodiments of the disclosure itself, as well as a preferred mode of use, further objectives and advantages thereof, will best be understood by reference to the following detailed description of an illustrative embodiment when read in conjunction with the accompanying drawings. One or more embodiments are now described, by way of example only, with reference to the accompanying drawings in which.

Figure 1:
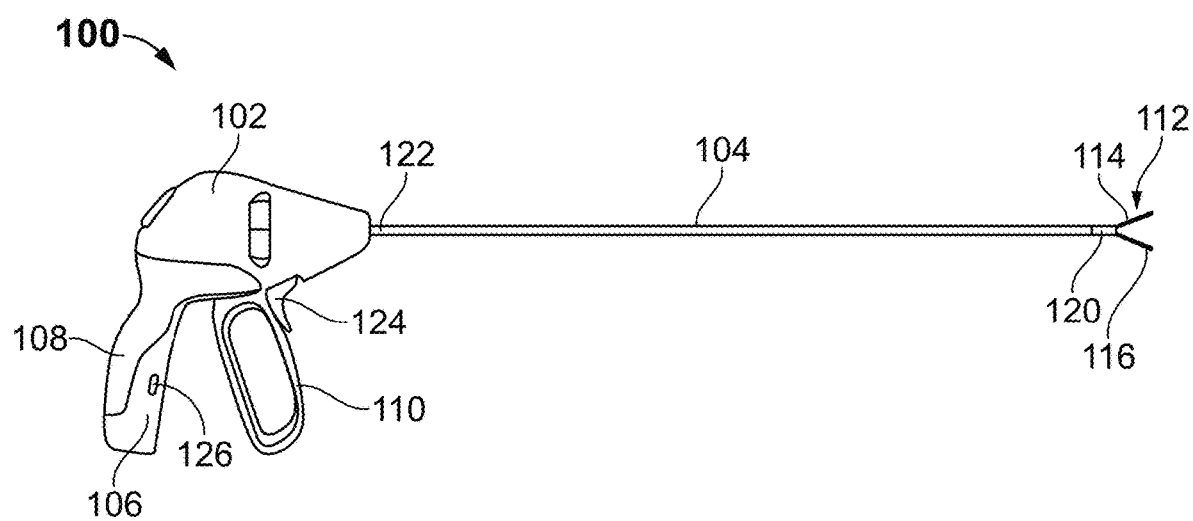
FIG. 1 illustrates an elevated view of endoscopic bipolar forceps with variable temperature control, in one embodiment.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the scope of the disclosure.

The terms "comprise", "comprising", "include(s)", or any other variations thereof, are intended to cover a non-exclusive inclusion, such that a setup, system or method that comprises a list of components or steps does not include only those components or steps but may include other components or steps not expressly listed or inherent to such setup or system or method. In other words, one or more elements in a system or apparatus proceeded by "comprises . . . a" does not, without more constraints, preclude the existence of other elements or additional elements in the system or apparatus.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Reference will now be made to the exemplary embodiments of the disclosure, as illustrated in the accompanying drawings. Wherever possible, same numerals will be used to refer to the same or like parts. Embodiments of the disclosure are described in the following paragraphs with reference to FIG. 1-FIG. 8.

Although the majority of the figure drawings depict bipolar forceps with variable temperature control 100 for use in connection with endoscopic surgical procedures, the present disclosure may be used for more traditional open surgical procedures. For the purposes herein, the forceps with variable temperature control 100 is described in terms of an endoscopic instrument, however, it is contemplated that an open version of the forceps with variable temperature control may also include the same or similar operating components and features as described below.

Bipolar vessel sealing technology uses a combination of electrical current and mechanical pressure to fuse vessel walls and create seals. The technology works by denaturing the collagen and elastin in the vessel walls with bipolar electrothermal energy, and then using mechanical pressure to form a coagulum. The system monitors the energy used while denaturing the collagen and elastin, and then re-cross links during the cooling phase to create a new seal. Bipolar devices may work under the control of actual temperature, monitoring impedance of the tissue to detect a seal, or both. When temperature of opposing electrodes (jaw members) reaches 100 degrees of Celsius, current delivery stops. Bipolar energy delivery in medical instrumentation is a technique that uses an electrical current to affect tissue between two active electrodes that are close together. The current is usually delivered at lower frequencies and settings, and can be used in situations where the surgical team wants to avoid burning or charring tissue.

Additionally, impedance of the tissue is monitored during sealing, where energy is controlled based upon the monitored impedance. In this embodiment, impedance is the tissue resistance of current introduced by the jaw members (electrodes) of the bipolar instrument. In this embodiment, the higher the resistance the higher energy is needed to allow the proper seal.

FIG. 1 illustrates a perspective view of endoscopic bipolar forceps with variable temperature and impedance control according to an embodiment of the present invention. The endoscopic bipolar forceps device 100 includes a housing 102 which is adapted to store electronic components (not shown) such as motor for operating the shaft 104. The housing 102 includes a handle 106 which is fixed to the housing 102 and includes an ergonomic grip 108 for safe and easy handling of the device 100 during operation. It is envisioned that the ergonomic grip 108 may include one or more protuberances, scallops and/or ribs to enhance gripping.

Figure 2:
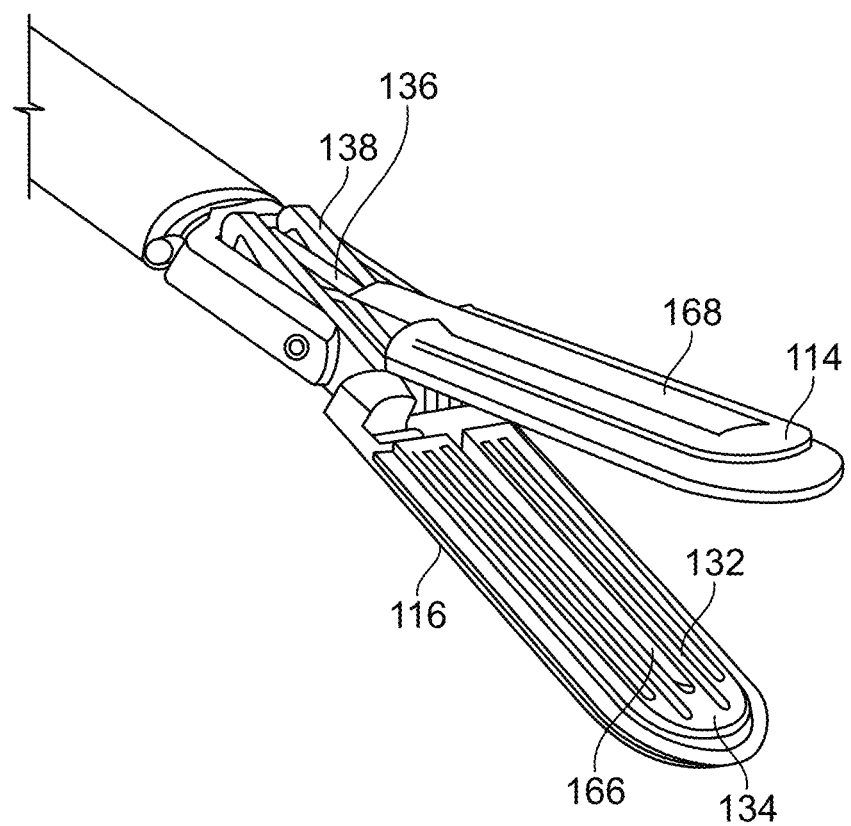
FIG. 2 illustrates a perspective view of the end effector assembly of the endoscopic bipolar forceps of FIG. 1.
Figure 3:
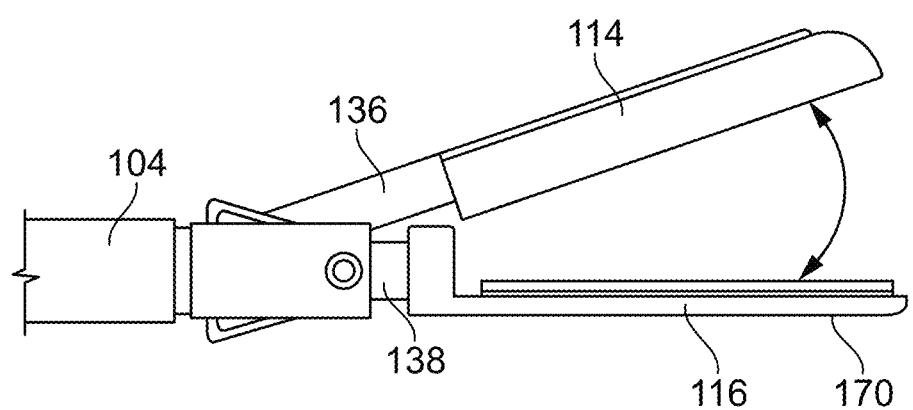
FIG. 3 illustrates an elevated view of one side of the end effector assembly of the endoscopic bipolar forceps of FIG. 2.
Figure 4:
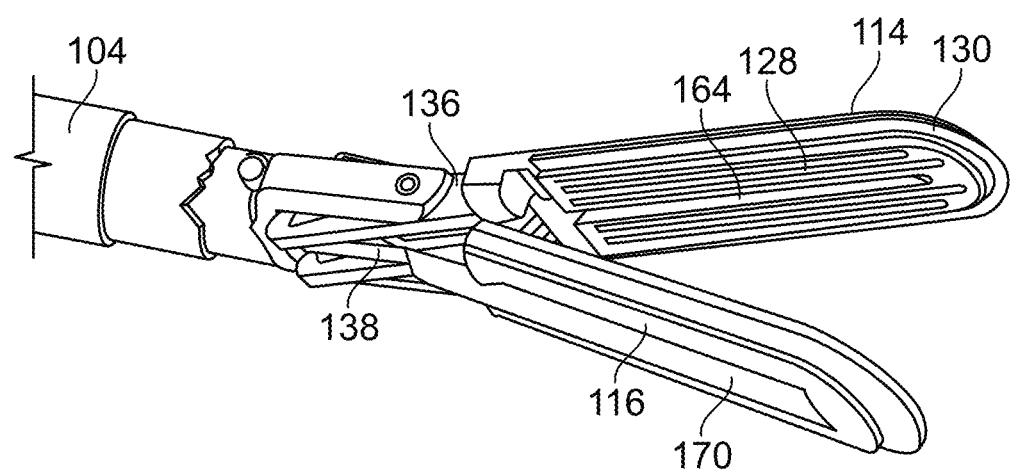
FIG. 4 illustrates a perspective view of another embodiment of the end effector assembly of the endoscopic bipolar forceps.
Figure 8:
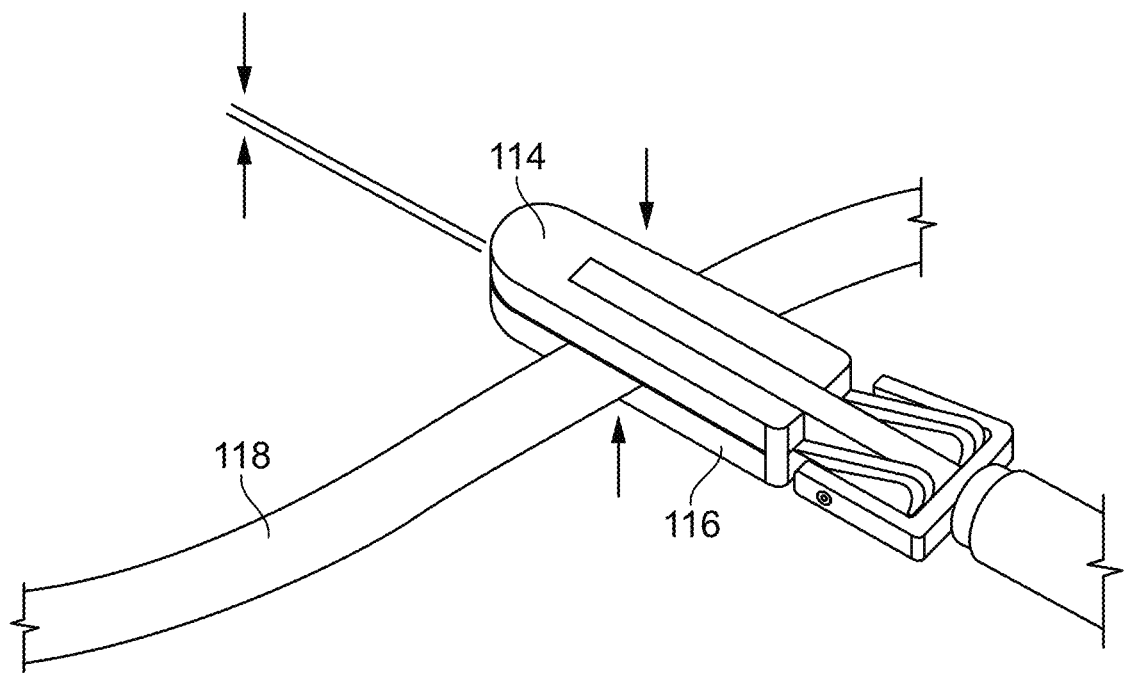
FIG. 8 illustrates an enlarged, rear, perspective view of the end effector assembly in a closed position grasping tissue, in accordance with an embodiment of the present disclosure.

A movable handle assembly 110 is pivotally disposed on the housing 102 and when actuated, operates the shaft 104 for using the end effector assembly 112. Referring to FIGS. 1-4, the end effector assembly 112 includes a pair of opposing jaw members 114,116. One of the opposing jaw members 114,116 is designed innovatively to include a plurality of individual electrode heat bars and the opposite jaw member 114 includes opposing recessed areas to each bar to accept the electrode heat bars when the opposing jaw members 114,116 are closed. The opposing jaw members 114,116 are adapted to transition between a closed or clamped position as illustrated in FIG. 8 wherein the opposing jaw members 114,116 are positioned to grasp a tissue or skin 118 and an open position as illustrated in FIGS. 2-4 where the tissue or skin 118 is not held between the opposing jaw members 114,116.

In the preferred embodiment, the end effector assembly 112 is removably attached to the distal end 120 of the shaft 104. In the drawings and in the descriptions which follow, the term "proximal," as is traditional, will refer to the end of the forceps with variable temperature control 100 which is closer to a user operating the device 100, while the term "distal" will refer to the end which is farther from the user. In the preferred embodiment, the end effector assembly 112 may be selectively and releasably engageable with the distal end 120 of the shaft 104 and/or the proximal end 122 of shaft 104 may be selectively and releasably engageable with the housing 102.

A trigger 124 is disposed on the movable handle assembly 110 and allows the opposing jaw members 114,116 to move between the closed position and the open position for an easy operation of the end effector assembly 112. A temperature control button 126 is disposed on the handle 106 and is electronically connected, either hard wire or wirelessly to a control unit 152 for monitoring impedance and performing temperature control of the electrode heat bars disposed in the jaw member 116 and recessed areas in the jaw member 114.

Referring now to FIG. 4, the first jaw member 114 includes a plurality of opposing recessed areas 128 disposed on the inner facing surface 130 of the jaw member 114. These recess members may also have applied heat in a same manner as electrode heat bars 132 in jaw member 116. Referring to FIG. 2, the second jaw member 116 includes a plurality of variable temperature electrode heat bars 132 disposed on the inner facing surface 134 of the jaw member 116. It is envisioned that jaw members 114 and 116 of end effector assembly 112 may be flat or curved to reach specific anatomical structures and promote more consistent seals for certain procedures.

More particularly, the end effector assembly 112 includes a first pivoting member 136 operatively coupled to the first jaw member 114 and a second pivoting member 138 operatively coupled to the second jaw member 116. The pivoting members 136,138 move on operation of the movable handle 110 to transition the jaw members 114,116 between the closed position and the open position.

Figure 6A:
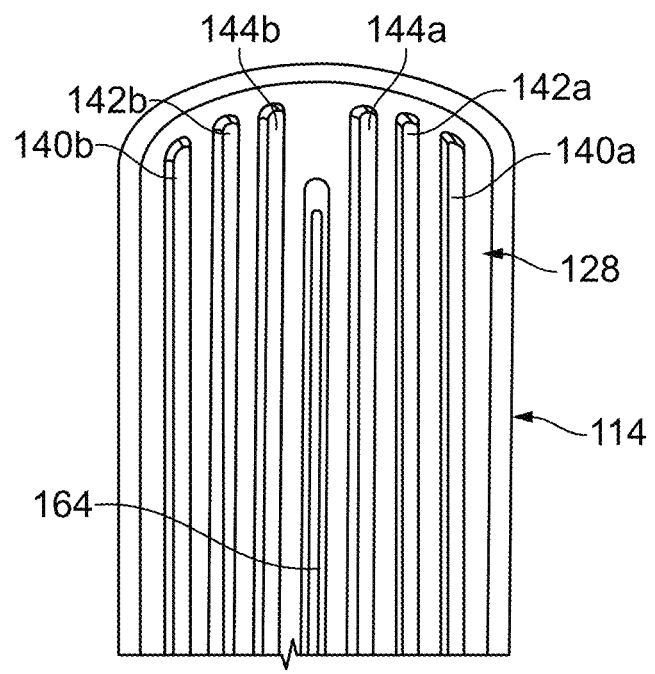
FIGS. 6A and 6B illustrate a top view of a pair of jaw members of the endoscopic bipolar forceps with variable temperature control.
Figure 6B:
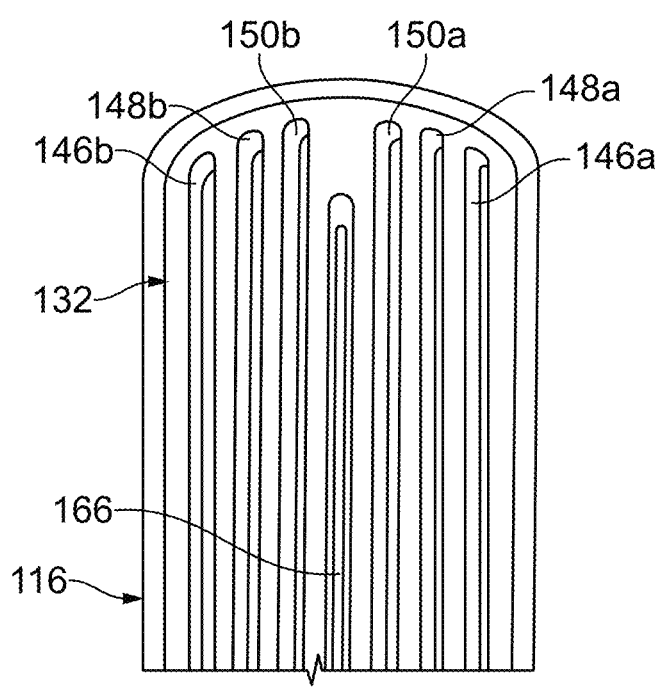

In the preferred embodiment, as illustrated in FIGS. 6A and 6B, the opposing recessed areas 128 of jaw member 114 include pairs of symmetrical recessed areas 140a, 140b, 142a, 142b, and 144a, 144b. Each pair of recessed areas may operate as a passive electrode in bipolar energy function discussed above and may have independent variable temperatures with 140a, and 140b having a different temperature than 142a, and 142b, for example. Each recess and each bar in the jaw members 114 and 116 may have independently controlled temperature and impedance sensing capability. Also, all the pairs comprising the recessed areas 128 on jaw member 114 or opposing bars on jaw member 116 may operate as one electrode detecting impedance and having a same temperature. The electrode heat bars 132 of jaw member 116 have a plurality of pairs of symmetrical electrode heat bars 146a, 146b, 148a, 148b, and 150a, 150b. Each pair of symmetrical electrode heat bars of the second jaw member 116 may have independent different temperatures or a same temperature. The individual recessed areas of the jaw member 114 are configured opposed to and accepting each corresponding electrode heat bar of the jaw member 116, thereby functioning as an opposing electrode. For example, 140a is opposed to 146a and is configured to accept the electrode heat bar 146a. Similarly, the recessed area 140b accepts 146b, 142a accepts 148a, 142b accepts 148b, 144a accepts 150a, and 144b accepts 150b.

The individual heat bars of the plurality of electrode heat bars 132 can have same length or can have different length for providing optimum heating and contact to veins, skin or other tissue of a user. Preferably, individual heat bar of each pair of electrode heat bars of the jaw member 116 have the same length and provides equal heat or temperature. The individual recessed area of the plurality of the recessed areas 128 also have same length as of the opposing electrode heat bars.

Figure 5:
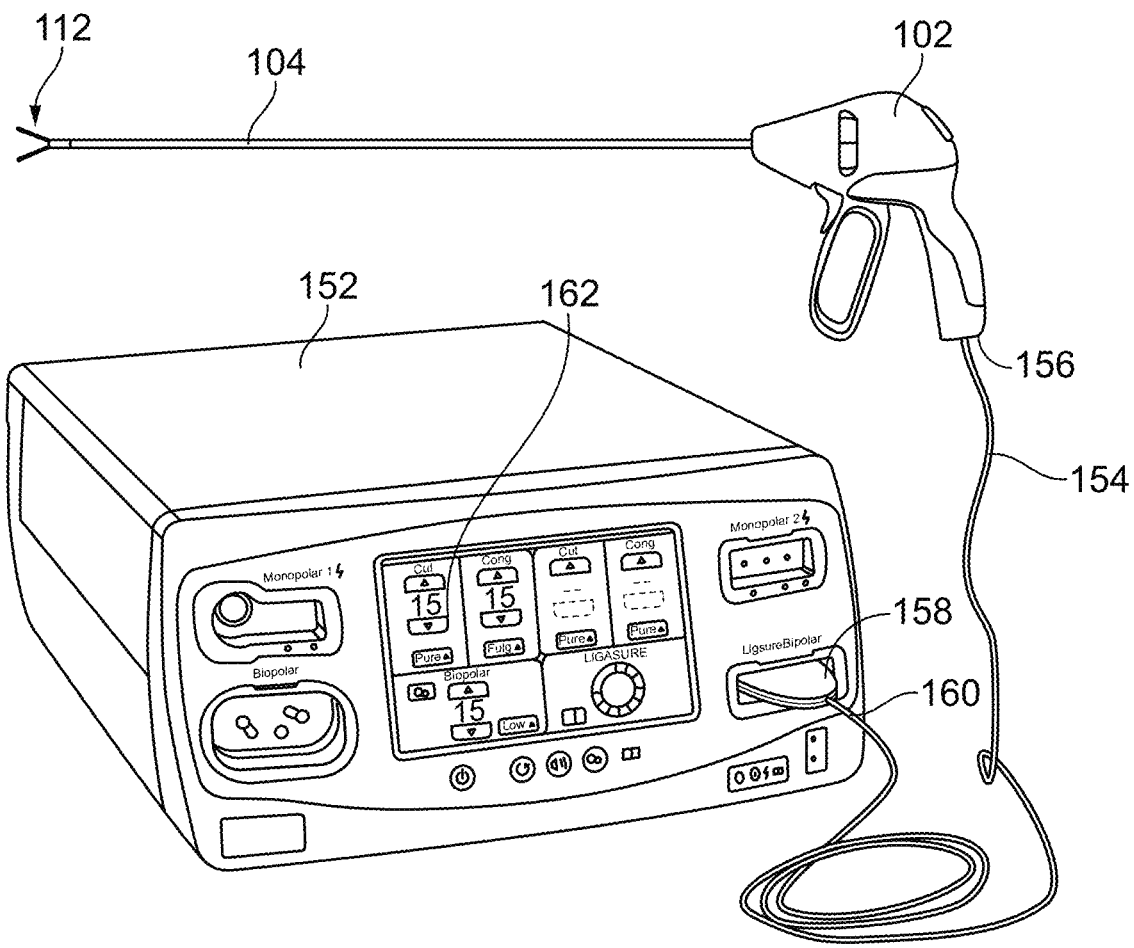
FIG. 5 illustrates a temperature control module used for temperature setting of the electrode heat bars of the end effector assembly in accordance with the disclosed structure.

Referring now to FIG. 5, a temperature control unit 152 is operatively connected to the device 100 using a control cable 154. The control cable 154 is integrated to the bottom end 156 of the housing 102 and includes a connector 158 at the opposite end 160 thereof. The controller 158 can be a serial connector and is detachably connected to the temperature control unit 152. Alternatively, control signal communication may be done with wireless transceivers at the device 102 and control unit 152. The temperature control unit 152 is adapted to provide controlled electric power to heat the electrode heat bars 128,132 disposed in the jaw members 114,116. The temperature control unit 152 is adapted to provide variable temperature to the individual electrode heat bars disposed in the jaw members 114,116. The temperature control unit 152 includes a display unit 162 that is configured to display temperature control settings of the individual bar pairs 146a, 146b, 148a,148b, and 150a, 150b and may display a graphic representation of the jaw members 114,116 indicating a temperature or temperature range that has been set for each pair. The cable 154 is internally divided into cable leads (not shown) which each transmit electrosurgical energy through their respective feed paths through the forceps with variable temperature control 100 to the end effector assembly 112 provide and maintain variable temperature to the individual electrode heat bars. In the preferred embodiment, each pair 146a,146b, 148a, 148b, and 150a, 150b of the symmetrical electrode heat bars is individually and independently controlled by the temperature control unit 152, thereby allowing an operator to individually control temperature of the pairs of the electrode heat bars of the jaw member 116.

The shaft 104 of the device 100 can have a length from about 35 cm to about 50 cm and the jaw members 114,116 can pivot forming an angle up to about 25 degrees relative to each other. The end effector assembly 112 is preferably disposable but may be reused after sanitisation in some embodiments of the present invention. Referring again to FIG. 6, the inner surfaces 130,134 of the jaw members 114,116 each include a cutting sleeve 164,166 for cutting the tissue 118 post sealing. The cutting sleeves 164,166 and the electrode heat bars 128,132 together facilitate sealing and cutting of tissue as illustrated in FIG. 8.

Figure 7:
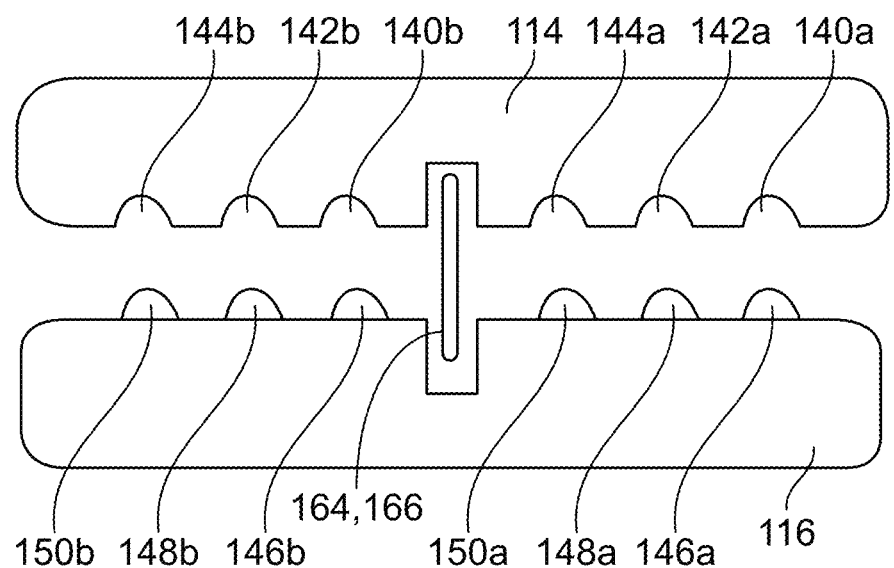
FIG. 7 illustrates front view of a plurality of bars in the pair of jaw members of the endoscopic bipolar forceps with variable temperature control with impedance monitoring, in accordance with an embodiment of the present disclosure.

Referring to FIG. 7, the corresponding electrode heat bars of the first jaw member 114 and the second jaw member 116 are symmetrically positioned allowing the corresponding electrode heat bars to heat and seal the skin as illustrated in FIG. 8. The cutting sleeves 164,166 are also symmetrically positioned to effectively cut skin for an efficient operation of the device 100. The top surface 168,170 of the jaw members 114,116 are preferably insulating and do not radiate heat of the heat members 128,132, thereby providing a safe operation for an operator of the device 100. Additionally, continued movement of the handle 110 causes the tissue to be sealed, and then engages cutting sleeves 164,166, which cuts the tissue.

It is envisioned that jaw members 114 and 116 of end effector assembly 112 may be curved in order to reach specific anatomical structures and promote more consistent seals for certain procedures. For example, it is contemplated that dimensioning the jaw members 114 and 116 at an angle of about 15 degrees to about 70 degrees may be preferred for accessing and sealing specific anatomical structures relevant to prostatectomies and cystectomies, e.g., the dorsal vein complex and the lateral pedicles. Other angles may be preferred for different surgical procedures.

In one embodiment, forceps with variable temperature control 100 include at least one tactile element or sensor which provides tactile feedback to the user to signify when tissue is being grasped, when the tissue has been sealed and/or when the tissue has been cut. Such a tactile element may include the turning on/off of lights (not shown) on housing 102 or mechanical vibrations being created in the fixed handle or movable handle. It is further envisioned for the sensor to be disposed on or within forceps with variable temperature control 100 to alert to the user when one or more completion stages has occurred, i.e., at the completion of tissue grasping, tissue sealing and/or tissue cutting.

A description of an embodiment with several components in communication with each other does not imply that all such components are required. On the contrary, a variety of optional components are described to illustrate the wide variety of possible embodiments of the disclosure. Further, there are other components also present in the substation communication network, however, these are not presented in the description to focus on the main features of the invention.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based here on. Accordingly, the embodiments of the present disclosure are intended to be illustrative, but not limiting, of the scope of the disclosure, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. An endoscopic bipolar forceps device, comprising:
    a housing;
    a shaft extending from the housing;
    a handle assembly pivotally disposed on the housing;
    an end effector assembly including a pair of opposing jaw members, one jaw member of the pair of opposing jaw members including a plurality of individual variable temperature electrode heat bars disposed linearly on an inner facing first planar surface of the jaw member, the other jaw member of the pair of opposing jaw members including a plurality of opposing individual variable temperature recessed areas disposed linearly on an inner facing second planar surface of the jaw member, each recessed area configured to accept a corresponding heat bar when the jaw members are in a closed position;
    a trigger on the handle assembly operatively connected to the opposing jaws to move them between closed and open positions; and
    a temperature control unit operatively connected to the electrode heat bars and to the individually variable temperature recessed areas to provide variable temperatures to separate individual electrode heat bars and recessed areas.

2. The device of claim 1, wherein the handle assembly includes a temperature control button for adjusting the temperature of the electrode heat bars and the recessed areas.

3. The device of claim 1, wherein the end effector assembly includes cutting sleeves disposed linearly, parallel to the electrode heat bars, on the first and second inner planar surfaces of the jaws for cutting tissue.

4. The device of claim 1, wherein the opposing jaws are pivotable to form an angle up to twenty-five degrees relative to each other.

5. The device of claim 1, wherein each heat bar of the plurality of electrode heat bars has the same length.

6. The device of claim 1, wherein each heat bar of the plurality of electrode heat bars has different length.

7. The device of claim 1, wherein the individually heated bars are made of a material that enhances thermal conductivity and ensures rapid heating and cooling.

8. An endoscopic bipolar forceps device, comprising:
    a housing with a handle including an ergonomic grip;
    a movable handle assembly pivotally disposed on the housing and operatively connected to a shaft;
    an end effector assembly detachably attached to a distal end of the shaft;
    a pair of opposing jaws within the end effector assembly, one jaw including a plurality of variable electrode heat bars disposed on an inner facing surface, and a second jaw including a plurality of opposing electrode recessed areas disposed on an inner facing surface, each opposing electrode recessed area configured to accept a corresponding electrode heat bar when the jaws are in a closed position, the electrode heat bars and electrode recessed areas being arranged symmetrically and enabled to measure impedance, introduce energy and detect temperature; and
    an impedance detection and temperature control unit enabled to control electric power to the electrode heat bars and electrode recessed areas while detecting impedance of tissue being sealed by the bipolar forceps device.

9. The device of claim 8, wherein the ergonomic grip includes protuberances, scallops, or ribs for enhancing gripping.

10. The device of claim 8, wherein each pair of symmetrical electrode heat bars are enabled to produce independent different temperatures.

11. The device of claim 8, wherein the shaft is selectively and releasably engageable with the housing.

12. The device of claim 8, wherein the end effector assembly is curved to reach specific anatomical structures and promote consistent seals.

13. An end effector assembly for an endoscopic bipolar forceps device, comprising:
- a first jaw member including a first inner surface and a second jaw member including a second inner surface;
- a plurality of variable energy electrode heat bars disposed linearly on the first inner surface of the first jaw member;
- a plurality of opposing electrode recessed areas disposed linearly on the second inner surface of the second jaw member, each recessed area configured to accept a corresponding electrode heat bar when the first and second jaw members are in a closed position;
- a first pivoting member operatively coupled to the first jaw member and a second pivoting member operatively coupled to the second jaw member enabling articulation of the first and second jaw members between an open and closed position;
- wherein the electrode heat bars and electrode recessed areas are configured to detect data including impedance of tissue held between the first and second jaw members and temperature at the bars, recessed areas and tissue, sending the data to a control unit, and the control unit controls an amount of energy implemented at the heat bars and recessed areas enabling consistent sealing and cutting of the tissue.

* * * * *